United States Patent [19]

Serbousek et al.

[11] Patent Number: 5,009,665
[45] Date of Patent: Apr. 23, 1991

[54] ACETABULAR CUP

[75] Inventors: Jon C. Serbousek; John A. Engelhardt, both of Warsaw, Ind.

[73] Assignee: Boehringer Mannheim Corp., Indianapolis, Ind.

[21] Appl. No.: 308,112

[22] Filed: Feb. 8, 1989

[51] Int. Cl.⁵ .............................................. A61F 2/34
[52] U.S. Cl. ................................................... 623/22
[58] Field of Search ................. 623/22, 23, 16, 18, 623/20

[56] References Cited

U.S. PATENT DOCUMENTS

| 4,530,116 | 7/1985 | Frey | 623/23 |
| 4,563,778 | 1/1986 | Roche et al. | 623/22 |
| 4,566,138 | 1/1986 | Lewis et al. | 623/22 |
| 4,666,450 | 5/1987 | Kenna | 623/22 |
| 4,695,282 | 9/1987 | Forte et al. | 623/22 |

FOREIGN PATENT DOCUMENTS 3714468 2/1988 Fed. Rep. of Germany ........ 623/22

Primary Examiner—Ronald Frinks
Attorney, Agent, or Firm—Max Kenemore

[57] ABSTRACT

An improved acetabular cup for use in cement fixation has at least one flat area on its generally hemispherical outer surface. The flat area resists rotation of the cup in the cement mantle after implantation while avoiding concentrations of stress in the mantle.

16 Claims, 1 Drawing Sheet

ACETABULAR CUP

FIELD OF THE INVENTION

The present invention relates generally to the field of implanted prosthetic human hips and more particularly to improved acetabular cups for use in cement fixation in the acetabulum.

BACKGROUND

Acetabular cups are well known as a component of prosthetic hips. The cup is inserted in the acetabulum in a prepared cavity and normally fixed in place by a cement mantle.

Loosening of the cup in the cement mantle and subsequent undesirable rotation of the cup in the mantle has long been a problem. Various techniques have been tried in the past to avoid this problem. For example, roughening of the outer surface of the cup to improve adhesion of the cement, the use of spacers to help form a cement mantle of uniform thickness, wire screens which are embedded in both the cement and the cup surface, patches of frit adhered to the cup's outer surface and angular protrusions to resist rotation have all been used with some degree of success.

The use of spacers or studs which are made of a material which is chemically compatible with the cement mantle is known. Coating of the outer surface of the cup with a material which is chemically compatible with the cement is also known. Cement-receiving grooves in the outer surface of the cup and in protrusions on the outer surface of the cup are also known and used.

However, breakdown of the cement mantel and a corresponding loosening of the acetabular cup in the mantel remains a problem. The problem causes pain and discomfort for patients in which the prosthetic acetabular cup has been installed. An installed hip in which the acetabular cup has come lose and rotates must normally be revised, requiring the patient to undergo further surgery.

A cup structure for use in cement fixation which will further reduce breakdown of the cement mantel and avoid the resulting rotation of the cup in the mantle is desirable.

SUMMARY OF THE INVENTION

It is an object of the present invention to avoid rotation of cement-fixed acetabular cup prosthetic implants.

It is also an object of this invention to avoid breakdown of the cement mantel in which an acetabular cup is fixed.

It is a further object of this invention to improve the life of installed human hip prosthetic devices.

These and other objects are accomplished by an improved acetabular cup for use in cement fixation to bone which comprises a hemispherical member having an internal recess which forms a bearing surface suitable for receiving a natural or prosthetic femoral head and a generally hemispherical outer surface on which there is at least one substantially flat area.

In a preferred embodiment the cup of the present invention has a plurality of circular flat areas and the margin where the hemispherical surface meets the flat surface is blended to avoid sharp edges.

The cup of this invention may be used in combination with previously known techniques such as spacers or studs, surface roughening and coating of the surface with a material which is chemically compatible with the cement used.

The cup of this invention may be formed in any useful embodiment. One such embodiment is a substantially hemispherical metal cup having a plurality of flat areas on its outer surface and having a bearing member retained by its inner surface such that the bearing member presents an internal bearing surface suitable for receiving the femoral head. The bearing member may be made of a low friction material such as high density polyethylene or certain ceramics.

Another example of a useful form of the invention is a one-piece substantially hemispherical cup having flat areas on its outer surface and an inner surface shaped to receive a femoral head wherein the cup is made entirely of a low friction material.

The invention is described below with reference to the drawings, which are intended to be illustrative and not exhaustive.

DETAILED DESCRIPTION

The present invention is based on the discovery that the flat areas, or negative voids, in the acetabular cups of the present invention present resistance to rotation of the cup in the cement mantle, probably due to the cement filling of the negative voids, while at the same time presenting lower concentrations of stress in the cement mantle than do cups which contain projections, grooves, flanges or other shapes which are designed to resist rotation of the cup in the mantle.

Figure 1:
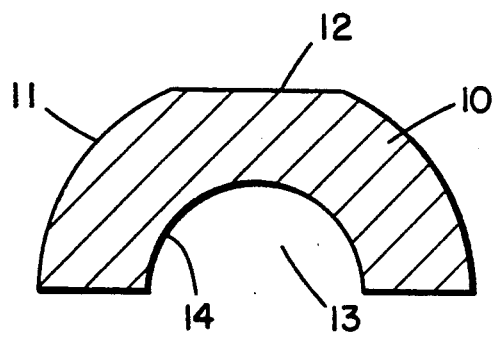
FIG. 1 shows a cross-sectional elevation of one embodiment of an acetabular cup according to the present invention.

FIG. 1 shows a cross-sectional view of a one-piece cup 10 according to the present invention. Such a cup can be made from any material which is biocompatable and which will articulate with a natural or prosthetic femoral head. For example cup 10 could be formed from a ceramic material or from a high density polyethylene which would provide both strength and low friction articulation with a femoral head.

Cup 10 has a substantially hemispherical outer surface 11 which contains a flat area 12. Cup 10 also has an internal recess 13 which presents a bearing surface 14 suitable for receiving a natural or prosthetic femoral head.

It will be immediately clear to one of ordinary skill in the technology that a flat area which presents the least amount of protrusion into a cement mantle around prosthesis will be round. In order to achieve a flat surface on the hemispherical surface which has any shape other than round would necessitate an edge between the flat area and the hemispherical surface which would protrude into the mantle. The protruding edge will result in concentrations of stress in the cement mantel. A circular flat area is preferred for this reason.

Figure 2:
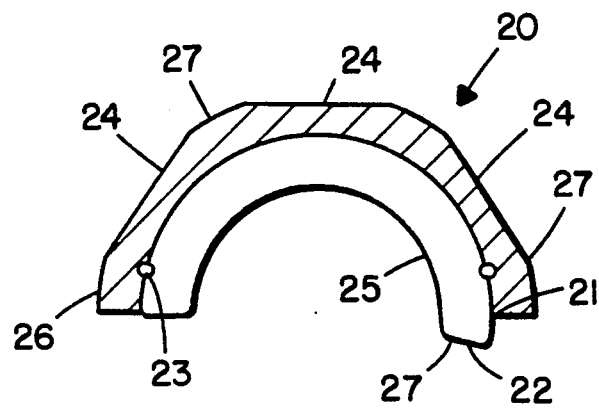
FIG. 2 shows a cross-sectional elevation of another embodiment of an acetabular cup according to the present invention.

FIG. 2 shows a cross-sectional elevation of another embodiment of the present invention in which cup 20 is formed from a metallic outer layer 21 and a polyethylene inner layer 22. In this embodiment the layers are held together by a metal O-ring 23, although any suitable method for holding the components together could be used. Layer 22 is shaped so as to provide lip 27 on one side of cup 20. The use of a lip such as lip 27 is a preferred embodiment of the cup of the present invention, especially when member 22 is rotationally adjustable within shell 21 so that the lip 27 can be positioned by the surgeon after the shell 21 has been fixed in place.

Outer layer 21 has on its surface flat areas 24. Inner layer 22 is shaped to form bearing surface 25 for receiving a natural or prosthetic femoral head. In the embodiment of FIG. 2 the flat areas, which are chords on hemispherical surface 26, should be sized so as to leave the shell thick enough to retain sufficient strength to be useful. The thickness will vary from material to material.

It is generally believed that a titanium alloy shell, for example, should have a minimum thickness of about 0.060 inch at the center of the flat areas in order to retain sufficient strength to be useful. In the size ranges of metal shells which are normal for acetabular cups, this thickness requirement will generally result in flat areas having a diameter of from about 0.430 inch to about 0.520 inch.

The cup of the present invention can be made by any well known method of manufacture suitable for the material chosen to be used. For example a metal shell can be cast or machined while high density polymers and ceramic materials dictate other methods of manufacture.

In a preferred embodiment the margins 27 where the substantially hemispherical surface 26 meets the flat surface 24 are blended to avoid sharp edges which might result in stress concentrations in a hardened cement mantle after implantation.

As is already well known in the art, the outer surface of the cup may be roughened to cause it to better adhere to the cement mantle.

Figure 3:
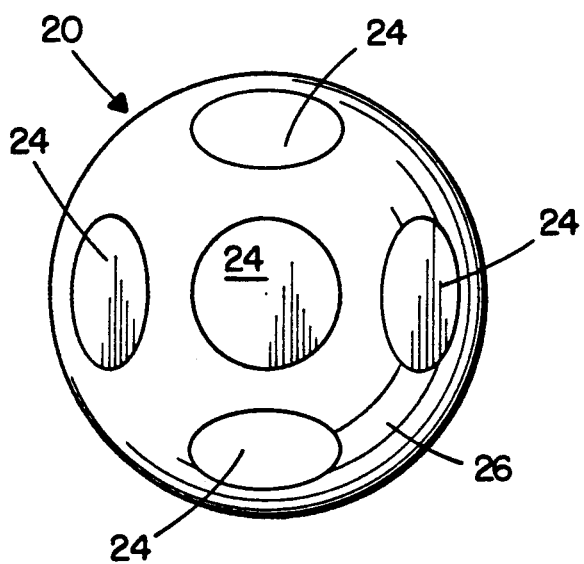
FIG. 3 shows a plan view of the cup of FIG. 2.

FIG. 3 shows a plan view of cup 20 of FIG. 2. Flat areas 24 are located at a variety of positions on the substantially hemispherical outer surface 26 of cup 20.

Figure 4:
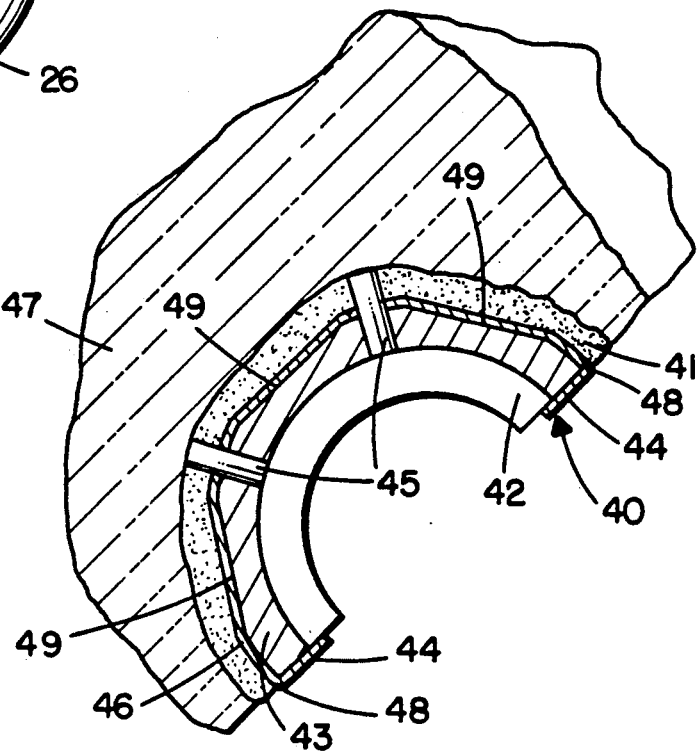
FIG. 4 shows a cross-sectional view of an acetabular cup according to the present invention after implantation.

FIG. 4 shows cup 40 of the present invention implanted in the acetabulum 47 of a patient by means of a cement mantel 41. In this embodiment bearing member 42 is held in place in the interior of shell 43 by means of flanges 44 on shell 43. Bearing member 42 is placed in shell 43 by first freezing it to cause it to shrink in size so that it can easily slip by flanges 44 and then allowing it to expand in place according to a well known process.

The embodiment of FIG. 4 employees studs 45 which extend from the substantially hemispherical surface 46 to act as spacers so that a relatively uniform thickness of cement forms cement mantel 41. The studs are made from a material which is chemically compatible with the material of mantel 41 and which readily adheres to the mantel or combines with it. The use of such spacers is well known in the art.

The embodiment of FIG. 4 also includes a thin layer 48 of material which is chemically compatible with the material in cement mantel 41 so as to promote adhesion between the layers.

Shell 43 includes flat areas 49 which form negative voids which are filled with cement mantel 41. The flat areas on shell 43 resist rotational movement of shell 43 in hardened mantel 41 without producing destructive concentrations of stress in the mantel.

The present invention has been disclosed in the above teachings and drawings with sufficient clarity and conciseness to enable one skilled in the art to make and use the invention, to know the best mode for carrying out the invention and to distinguish it from other inventions and from what is old. Many variations and obvious adaptations of the invention will readily come to mind, and these are intended to be contained within the scope of the invention as claimed below.

What is claimed is:

1. An improved acetabular cup prosthesis for use in cement fixation to bone, said cup comprising a hemispherical member having an internal recess which forms a bearing surface suitable for receiving a natural or prosthetic femoral head and a generally hemispherical outer surface on which there is at least one substantially flat area displaced from the apex of the cup and within the cross-sectional profile of the hemispherical surface.

2. The prosthesis of claim 1 wherein the substantially flat area is substantially circular.

3. The prosthesis of claim 1 wherein there is a plurality of flat areas.

4. The prosthesis of claim 1 wherein the margin between the flat portion of the outer surface and the substantially hemispherical portion of the outer surface is blended.

5. The prosthesis of claim 1 wherein the outer surface is treated.

6. The prosthesis of claim 5 wherein the surface is treated by roughening.

7. The prosthesis of claim 1 wherein spacers are used to determine the standoff between the prosthesis surface and bone into which it is implanted.

8. An improved acetabular cup prosthesis for use in cement fixation to bone, said cup comprising a hemispherical shell having on its outer surface at least one flat area which is displaced from the apex of the cup and which is within the cross-sectional profile of the cup and having retained internally a bearing member which is shaped to provide an internal bearing surface suitable for receiving a natural or prosthetic femoral head.

9. The prosthesis of claim 8 wherein the substantially flat area is substantially circular.

10. The prosthesis of claim 8 wherein there is a plurality of flat areas.

11. The prosthesis of claim 8 wherein the margin between the flat portion of the outer surface and the substantially hemispherical portion of the outer surface is blended.

12. The prosthesis of claim 8 wherein the outer surface is treated.

13. The prosthesis of claim 12 wherein the surface is treated by roughening.

14. The prosthesis of claim 8 wherein spacers are used to determine the standoff between the prosthesis surface and bone into which it is implanted.

15. The prosthesis of claim 8 wherein the shell is metal.

16. The prosthesis of claim 8 wherein the bearing member is a polymer.

* * * * *